(12) United States Patent
Tracy

(10) Patent No.: US 7,431,716 B2
(45) Date of Patent: Oct. 7, 2008

(54) DISPOSABLE DIAPER HAVING REMOVABLE CORE

(76) Inventor: Rhonda Tracy, 233 Grandview Ave., Glen Ellyn, IL (US) 60137

( * ) Notice: Subject to any disclaimer, the term of this patent is extended or adjusted under 35 U.S.C. 154(b) by 934 days.

(21) Appl. No.: 10/931,331

(22) Filed: Sep. 1, 2004

(65) Prior Publication Data
US 2005/0049569 A1 Mar. 3, 2005

Related U.S. Application Data

(60) Provisional application No. 60/499,546, filed on Sep. 2, 2003.

(51) Int. Cl.
*A61F 13/20* (2006.01)
(52) U.S. Cl. .............. 604/385.14; 604/385.01; 604/385.11
(58) Field of Classification Search ............ 604/385.14, 604/385.01, 385.11, 385.15, 378, 397; 119/169, 119/171
See application file for complete search history.

(56) References Cited

U.S. PATENT DOCUMENTS

| 4,019,517 | A | * | 4/1977 | Glassman | 604/394 |
| 4,265,245 | A | * | 5/1981 | Glassman | 604/365 |
| 4,578,073 | A | * | 3/1986 | Dysart et al. | 604/397 |
| 5,217,447 | A | * | 6/1993 | Gagnon | 604/397 |
| 5,360,422 | A | * | 11/1994 | Brownlee et al. | 604/385.15 |
| 5,405,342 | A | * | 4/1995 | Roessler et al. | 604/364 |
| 2001/0143316 | | * | 10/2002 | Sherrod et al. | 604/385.101 |

FOREIGN PATENT DOCUMENTS

WO WO 91/16871 * 11/1991

* cited by examiner

*Primary Examiner*—Tatyana Zalukaeva
(74) *Attorney, Agent, or Firm*—Barnes & Thornburg LLP

(57) ABSTRACT

A disposable diaper having a diaper body including an inner lining comprising a liquid-absorbent material and a removable core shaped to engage a portion of the inner lining. The removable core is temporarily secured to the diaper body and is removable therefrom.

16 Claims, 2 Drawing Sheets

DISPOSABLE DIAPER HAVING REMOVABLE CORE

RELATED APPLICATION

This application is the nonprovisional filing of U.S. provisional application No. 60/499,546 filed Sep. 2, 2003.

BACKGROUND OF THE INVENTION

This invention relates to disposable diapers, and in particular to a disposable diaper having a separate and removable core.

Disposable diapers are in wide use in the United States and throughout the world, having largely replaced cloth diapers worn by infants and toddlers. Disposable diapers not only can be easily discarded when soiled, but are adjustable, convenient to attach, and easily removed. Disposable diapers are typically capable of effective retention of both liquid and solid material without having a separate protective cover, as was required by cloth diapers.

While disposable diapers are quite effective, one problem is the necessity to dispose of the entire diaper, even when lightly soiled. Being able to reuse a lightly soiled diaper while still eliminating soiling would be a great advantage.

SUMMARY OF THE INVENTION

The invention is directed to a disposable diaper comprising a diaper body, the diaper body having an inner lining comprising a liquid-absorbent material and the diaper body being shaped so that the diaper may extend about the waist and crotch of a wearer with the inner lining towards the wearer. A removable core is provided, shaped to engage a portion of the inner lining. The removable core has a liner comprising a liquid-absorbent material. Means is provided for joining the removable core and the diaper as a unit.

In accordance with one form of the invention, the joining means comprises a connector. The connector may comprise a plurality of spaced fasteners, with those fasteners, in one form of the invention, comprising adhesive materials. While any type of adhesive material can be employed, adhesive materials such as glue, paste, cement and tape can be used. In another form of the invention, the fasteners comprise hook-and-loop fasteners.

In another form of the invention, the joining means comprises a frictional engagement of the removable core and the diaper body. In one form, that frictional engagement may comprise an indentation in the inner lining with the removable core being shaped to fit within the indentation. In another form, the frictional engagement comprises adhesion of the removable core and the inner lining to one another.

In all forms of the invention, preferably the removable core includes a liquid barrier layer secured to the liner, so that light soiling of the liner does not then migrate to the inner lining of the diaper body, while heavy soiling is accommodated by the lining of the diaper body, in a conventional fashion.

The removable core may be sized as desired to occupy as little or as much of the inner lining of the diaper body. Preferably, the removable core is sized to engage at least the crotch of the wearer.

BRIEF DESCRIPTION OF THE DRAWINGS

The invention is described in greater detail in the following description of examples embodying the best mode of the invention, taken in conjunction with the drawing figures, in which.

DESCRIPTION OF EXAMPLES EMBODYING THE BEST MODE OF THE INVENTION

Figure 1:
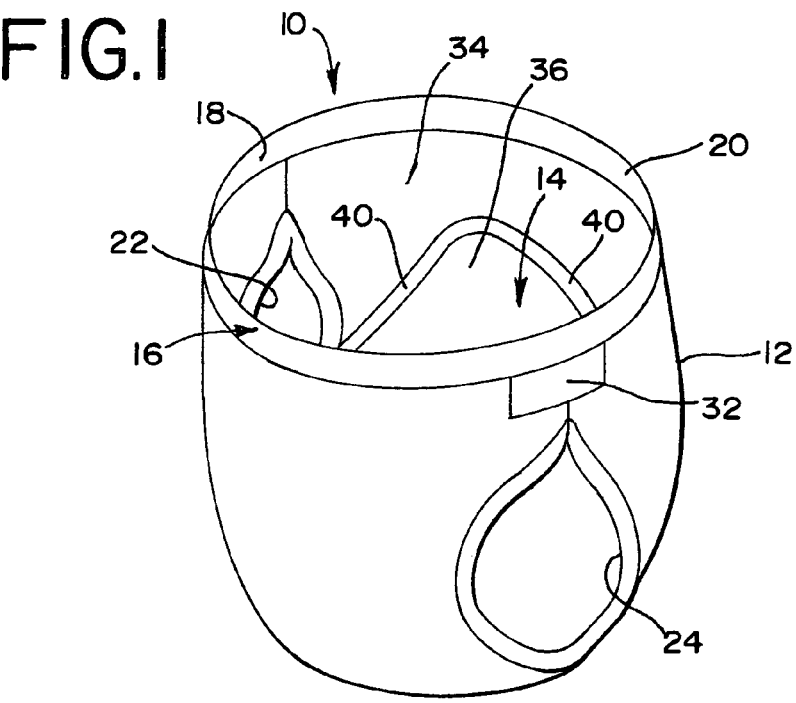
FIG. 1 is a perspective view of a disposable diaper according to the invention, when formed about a wearer, but with the wearer being omitted to illustrate detail.
Figure 2:
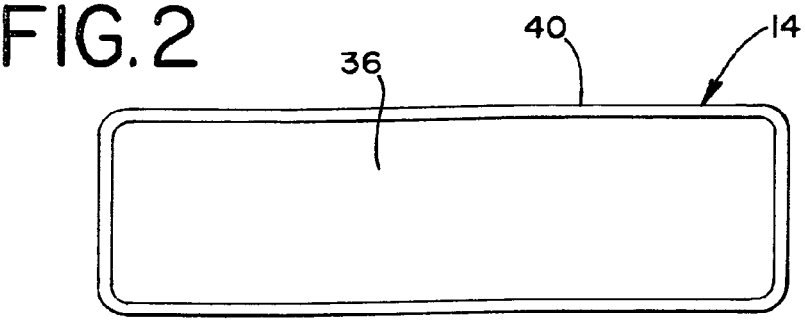
FIG. 2 is a top plan view of a disposable core according to the invention.
Figure 3:
FIG. 3 is a cross sectional view of the disposable core according to the invention.
Figure 4:
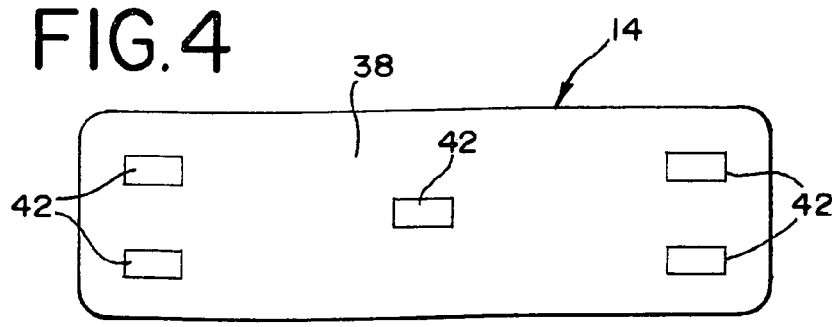
FIG. 4 is a bottom plan view of a disposable core according to the invention.

A diaper according to the invention is shown generally at 10 in the drawing figures. The diaper 10 comprises two basic elements, a diaper body 12 and a removable core 14.

Figure 5:
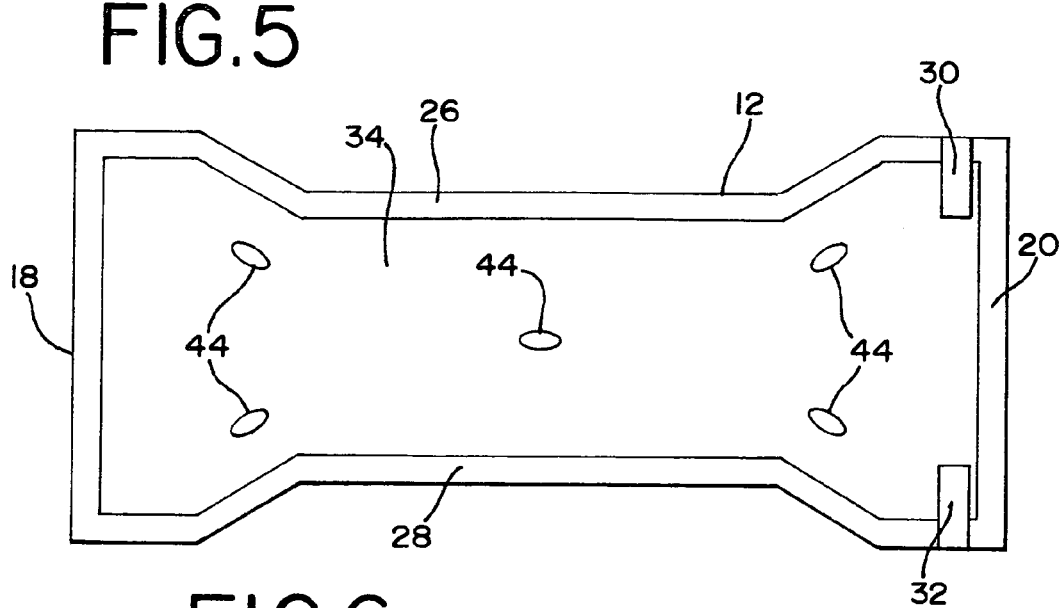
FIG. 5 is a top plan view of a disposable diaper according to the invention when unfolded, and without the removable core in place.

The diaper body 12 can be conventional, and may be in accordance with applicant's U.S. Pat. No. 5,797,824 and/or applicant's earlier U.S. Pat. No. 5,064,421. The diaper body 12, as in its closed configuration shown in FIG. 1, may include a padded waistline 16 formed of waist sections 18 and 20 (best shown in FIGS. 5 and 6), and padded leg holes 22 and 24 which are formed when the diaper body 12 is in the closed configuration. A padded peripheral section 26 (FIGS. 5 and 6) of the diaper body 12 forms the leg hole 22, and a padded peripheral section 28 forms the leg hole 24. A pair of adhesive strips 30 and 32 (FIGS. 5 and 6) is used for securing the diaper to a wearer in a conventional fashion. Alternatively, of course, the diaper 10 may be provided in an already "assembled" manner with a continuous waistband and preformed leg holes, as will be quite evident to one skilled in the art.

The diaper body 12 also includes an inner lining 34 which comprises a liquid-absorbent material. The inner lining 34 may be conventional, and can be formed of multiple layers of material as is well known in the art. As is typical, the inner lining 34 occupies essentially the entire inner surface of the diaper body 12 when formed as the diaper 10.

Figure 6:
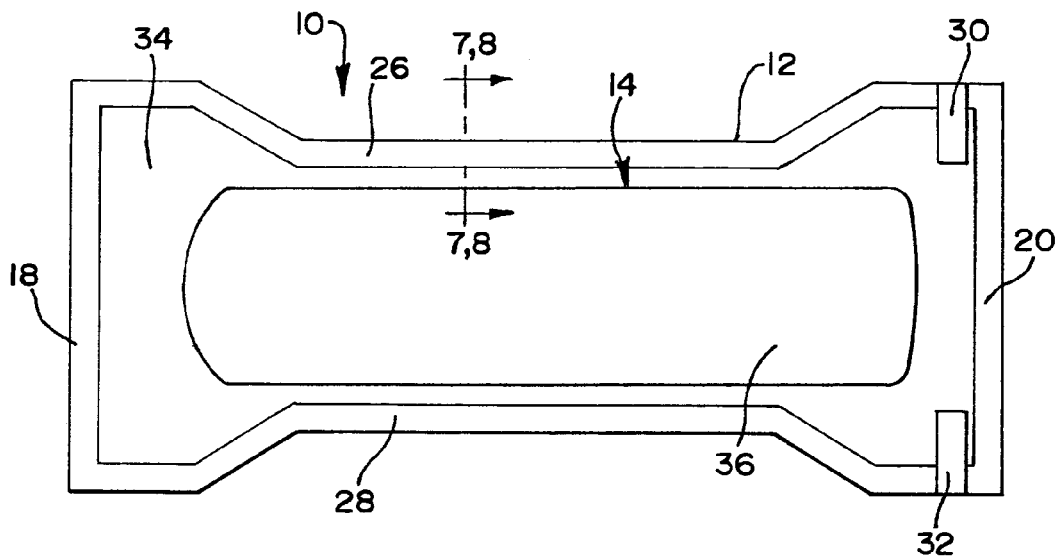
FIG. 6 is a view similar to FIG. 5, but with the removable core in place.

The removable core 14 is shaped to engage a portion of the inner lining 34, as best shown in FIG. 6. The removable core 14 includes a liner 36 comprising a liquid-absorbent material, which may be identical to the liquid-absorbent material of the inner lining 34. Although not mandatory, preferably the removable core 14 also includes a liquid barrier layer 38 so that any liquid impinging on the removable core 14 can be retained by the removable core to the extent of the holding capacity of the removable core. The liquid barrier layer 38 extends coextensively with all portions of the removable core 14 that may be in contact with the inner lining 34, and can include a peripheral edge portion 40 extending about that portion of the liner 36 contacting the wearer.

It is preferred that the removable core 14 be maintained in place in relation to the inner lining 34. This may be done in many different ways. For example, various types of connectors can be employed to removeably hold the core 14 in place. In this form of the invention, preferably, a plurality of spaced fasteners 42, secured to the underside of the removable core 14 (and thus to the barrier layer 38), are used. While five such fasteners are illustrated, any number of fasteners appropriate to hold the removable core 14 in place can be employed. The fasteners 42 can be adhesive materials, such as glue, paste, cement, tape or any other attachable material. For proper adhesion to the inner lining 34, corresponding target points or pellets 44 may be located in a spaced fashion on the inner lining 34 to assure proper adhesion, although in most instances the target points or pellets 44 will be unnecessary.

Rather than be made of an adhesive material, the spaced fasteners 42 can, alternatively, be formed of a hook-and-loop material or any other type of fabric fastener to hold the removable core in place. Other means of fastening of this nature will be apparent to those skilled in the art.

Figure 7:
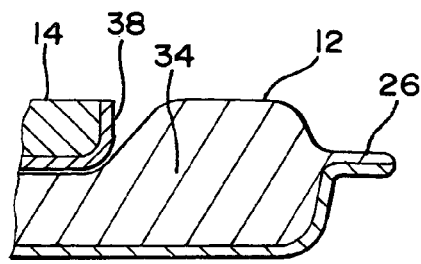
FIG. 7 is a cross sectional view taken along lines 7-7 of FIG. 6 showing one form of accommodation of the disposable core.

In another form of the invention, the removable core 14 is joined to the inner lining 34 of the diaper body 12 by means of frictional engagement. The material of the liquid barrier layer 38 and the material of the inner lining 34 are selected such that there is an affinity of the materials, forming a temporary adhesion so that the removable core 14 may be easily peeled away from the inner lining 34. This is shown schematically in FIG. 7.

Figure 8:
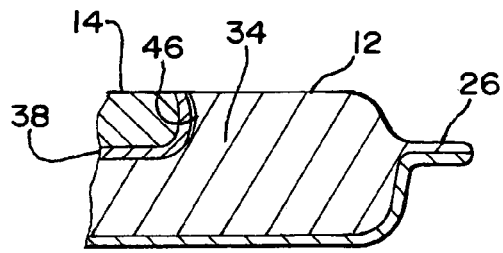
FIG. 8 is a cross sectional view taken along lines 8-8 of FIG. 6 showing another form of accommodation of the disposable core.

Another form of frictional engagement between the removable core 14 and the inner lining 34 may be forming the inner lining 34 with an indentation or cavity 46 in which the removable core 14 is lodged, as shown in FIG. 8. In this form of the invention, the dimensions of the removable core 14 and the indentation or cavity 46 are essentially identical so that the removable core 14 fits snugly within the indentation or cavity 46.

The diaper 10 therefore comprises a two element structure, the diaper body 12 and the removable core 14. The removable core 14 can therefore be removed and discarded separately from the diaper 12. Thus, when only the removable core 14 is soiled during use, it can be removed and the original diaper may then continue to be used a "second" time, thus promoting conservation of resources and reduction of cost.

The removable core 14 is shown as being in a generally rectangular form in the drawing figures. The removable core 14 can be of any shape appropriate for liquid absorption, and preferably is sized to engage at least the crotch area of the wearer of the diaper 10. The size and shape of the removable core 14 can be dictated by many factors, among them comfort, liquid and solid holding capacity, and compatibility with the surrounding shape of the diaper body 12. Also, the material forming the liner 36 may be the same as or different from the material forming the, inner lining 34, as needs dictate.

While the invention has been described in relation to a disposable diaper, it will be evident that the invention is usable in diapers, training pants or briefs, and can be used for any age wearer, from infant to adult. Various changes can be made to the invention without departing from the spirit thereof or scope of the following claims.

The invention claimed is:

1. A disposable diaper, comprising
   a. a diaper body, said diaper body having an inner lining comprising a liquid-absorbent material and said diaper body being shaped so that the diaper may extend about a waist and crotch of a wearer with the inner lining toward the wearer,
   b. a removable core shaped to engage a portion of said inner lining, said removable core having a liner comprising a liquid-absorbent material, and a liquid barrier layer substantially coextensive with said removable core, forming a liquid-impervious boundary between said core and said liquid absorbent material,
   c. an indentation in said inner lining and said removable core being shaped to fit within said indentation, and
   d. means joining said removable core and said diaper body.
2. The disposable diaper according to claim 1, in which said joining means comprises rises a connector.
3. The disposable diaper according to claim 2, in which said connector comprises a plurality of spaced fasteners.
4. The disposable diaper according to claim 3, in which said fasteners comprise adhesive materials.
5. The disposable diaper according to claim 4, in which said adhesive materials are selected from the group comprising glue, paste, cement and tape.
6. The disposable diaper according to claim 3, in which said fasteners comprise hook-and-loop fasteners.
7. The disposable diaper according to claim 1, in which said joining means comprises a frictional engagement of said removable core and said diaper body.
8. The disposable diaper according to claim 7, in which said frictional engagement comprises adhesion of said removable core and said inner lining to one another.
9. The disposable diaper according to claim 1, in which said removable core is sized to engage at least the crotch of the wearer.
10. A disposable diaper, comprising
    a. a diaper body, said diaper body having an inner lining comprising a liquid-absorbent material and said diaper body being shaped so that the diaper may extend about a waist and crotch of a wearer with the inner lining toward the wearer,
    b. a removable core shaped to engage a portion of said inner lining, said removable core having a liner comprising a liquid-absorbent material and a liquid barrier layer secured to said core and substantially coextensive therewith, forming a liquid-impervious boundary between said core and said liquid absorbent material,
    c. an indentation in said inner lining and said removable core being shaped to fit within said indentation, and
    d. an engagement of said removable core to said diaper body.
11. The disposable diaper according to claim 10, in which said engagement comprises a plurality of spaced fasteners.
12. The disposable diaper according to claim 11, in which said fasteners comprise adhesive materials.
13. The disposable diaper according to claim 12, in which said adhesive materials are selected from the group comprising glue, paste, cement and tape.
14. The disposable diaper according to claim 11, in which said fasteners comprise hook-and-loop fasteners.
15. The disposable diaper according to claim 10, in which said engagement comprises a frictional engagement of said removable core and said diaper body.
16. The disposable diaper according to claim 15, in which said frictional engagement comprises adhesion of said removable care and said inner lining to one another.

* * * * *